(12) United States Patent
Tomar et al.

(10) Patent No.: US 8,156,812 B2
(45) Date of Patent: Apr. 17, 2012

(54) METHOD FOR NON-DESTRUCTIVE INSPECTION

(75) Inventors: Munendra S. Tomar, Houston, TX (US); Martin Fingerhut, League City, TX (US); Deli Yu, Edmonton (CA)

(73) Assignee: Röntgen Technische Dienst B.V., Rotterdam (NL)

( * ) Notice: Subject to any disclaimer, the term of this patent is extended or adjusted under 35 U.S.C. 154(b) by 529 days.

(21) Appl. No.: 12/379,944

(22) Filed: Mar. 4, 2009

(65) Prior Publication Data

US 2009/0229362 A1 Sep. 17, 2009

Related U.S. Application Data

(60) Provisional application No. 61/064,422, filed on Mar. 5, 2008.

(51) Int. Cl.
G01N 29/04 (2006.01)
G01N 21/00 (2006.01)

(52) U.S. Cl. ............... 73/602; 73/620; 73/622

(58) Field of Classification Search ........... 73/618–620, 73/601–602, 622–625, 596–600
See application file for complete search history.

(56) References Cited

U.S. PATENT DOCUMENTS 3,910,124 A * 10/1975 Halsey ............... 73/601
4,866,614 A * 9/1989 Tam ............... 600/437
5,996,413 A * 12/1999 Iyer et al. ............... 73/592
6,062,084 A 5/2000 Chang et al.
7,153,185 B1 12/2006 Birang

FOREIGN PATENT DOCUMENTS

DE 103 26 217 12/2004
WO WO 2008/031423 3/2008

OTHER PUBLICATIONS

"Device rotates bearing balls for inspection," NTIS Tech Notes, U.S. Department of State Commerce, pp. 46 (Jan. 1, 1989).
International Search Report dated Mar. 5, 2008.

* cited by examiner

Primary Examiner — Helen C. Kwok
(74) Attorney, Agent, or Firm — Jacobson Holman PLLC (57) ABSTRACT

Method for non-destructive inspection of defects in a surface of a pipeline or storage tank. The method includes carrying out a first way of non-destructive inspection for determining a first defect pattern and carrying out a second way of non-destructive inspection for determining a second defect pattern. The method includes identifying at least one defect of the first defect pattern and at least one defect of the second defect pattern which represent one and the same defect, and comparing the dimensions and optionally also the positions of the identified defects so as to obtain a difference in dimensions and optionally also in the positions. The method also includes obtaining a plurality of such differences and obtaining at least one parameter representing said differences, and correcting the dimensions and optionally also the positions of defects of the first defect pattern by using the at least one parameter.

40 Claims, 4 Drawing Sheets

METHOD FOR NON-DESTRUCTIVE INSPECTION

This is a complete application claiming benefit of U.S. provisional application No. 61/064,422, filed Mar. 5, 2008, hereby incorporated by reference.

BACKGROUND OF THE INVENTION

The invention relates to a method for non-destructive inspection of defects in a surface of a pipeline or storage tank for hydrocarbon transport or storage.

In a known method of pipeline or tank inspection, for example based on Magnetic Flux Leakage (MFL), an in-line inspection tool is moved along for example the pipeline. Defect patterns determined by such a method in general provide information about defect dimensions and defect locations in a surface of the pipeline. Mitigation plans, such as repair and replacement of the pipeline, are based on the defect patterns. However, usually there is a systematic error related to the defect patterns, giving rise to insecurity about for example a failure pressure of the pipeline. Because failure of the pipeline must be prevented, interpretation of the inspection results for mitigation plans is rather conservative. This may drive up a number of digs in a pipeline rehabilitation project and often give rise to unnecessary costs.

BRIEF SUMMARY OF THE INVENTION

It is an objective of the invention to provide a method for correcting defect patterns resulting from non-destructive inspection.

The invention provides a method for non-destructive inspection of defects in a surface of a pipeline or storage tank for hydrocarbon transport or storage, including the steps of: a) carrying out a first way of non-destructive inspection of a first part of the surface by moving a first inspection tool along the first part of the surface for determining a first defect pattern that includes dimensions and positions of defects in the first part of the surface; b) carrying out a second way of non-destructive inspection of a second part of the surface by moving a second inspection tool along the second part of the surface for determining a second defect pattern that includes dimensions and positions of defects in the second part of the surface, wherein the total area of the second part of the surface is smaller than the total area of the first part of the surface and the second part of the surface overlaps with the first part of the surface, and wherein a systematic error of the second way of non-destructive inspection is smaller than a systematic error of the first way of non-destructive inspection; c) identifying at least one defect of the first defect pattern and at least one defect of the second defect pattern which represent one and the same defect; d) comparing the dimensions and optionally also the positions of the identified defects in step c) which represent one and the same defect so as to obtain a difference in dimensions and optionally also the positions measured with the first way of non-destructive inspection and the second way of non-destructive inspection respectively; e) repeating steps c) and d) so as to obtain a plurality of differences and obtaining at least one parameter representing said differences; and f) correcting the dimensions and optionally also the positions of defects of the first defect pattern by using the at least one parameter obtained in step e).

Such a method has the advantage that the systematic measurement error of the first way of non-destructive inspection can at least partly be corrected. In this way a decision on mitigation of the pipeline or storage tank can be less conservative. This allows operators of the pipeline or storage tank to target maintenance activities more efficiently. In this way, the operators of the pipeline or storage tank can also better predict corrosion growth rates and optimize time intervals from a moment of inspection to a subsequent moment of inspection. Also, a better failure pressure of the pipeline or storage tank, for example as a result of a fluidum pressure inside the element, can be predicted. The second part of the surface is substantially smaller than the first part of the surface. Preferably, a time and/or cost needed for step b) is substantially smaller than a time and/or cost needed for step a).

Preferably, the first and second way of non-destructive inspection are carried out substantially automatically, so that errors as a result of manual inspection are substantially prevented.

Preferably, the first way of non-destructive inspection includes using Magnetic Flux Leakage measurements. This method can yield relevant measurements relatively quickly over a large part of the pipeline or storage tank. Preferably, the second way of non-destructive inspection includes inspection by means of a laser, preferably laser profilometry. This method can yield a relatively accurate measurement having a relatively small systematic error.

In particular, the method according to the invention includes classifying the defects of the first defect pattern and optionally the defects of the second defect pattern in a plurality of defect categories. In this way, correcting in f) can be carried out separately for each category. More in particular, the classification of the defects of the first defect pattern and the optional classification of the defects of the second defect pattern in the plurality of defect categories is based on the dimensions of the defects. As a result, correcting in f) can be carried out in dependence on the defect dimensions, such as a length, width, depth and/or shape of the defect.

More preferably, the method includes validating the at least one parameter. This has the advantage that it is checked that a corrected first defect pattern after correcting in f) is indeed more reliable than the uncorrected first defect pattern. Such validating may include the steps of:

g) carrying out the second way of non-destructive inspection for a third part of the pipeline by moving a second inspection tool along the third part of the surface for determining a third defect pattern that includes dimensions and positions of defects in the third part of the surface, wherein the total area of the third part of the surface is smaller than the total area of the first part of the surface, the third part of the surface overlaps with the first part of the surface and wherein the third part differs from the second part;

h) identifying at least one defect of the corrected first defect pattern and at least one defect of the third defect pattern which represent one and the same defect;

i) comparing the dimensions and optionally also the positions of the identified defects in step h) which represent one and the same defect so as to obtain a difference in dimensions and optionally also in the positions measured with the first way of non-destructive inspection and the second way of non-destructive inspection respectively;

j) repeating steps h) and i) so as to obtain a plurality of differences; and k) verifying that the differences obtained in step j) are generally smaller than the differences obtained in step e) in accordance with a statistic criterium.

In a relevant variation of the invention, the element is a buried pipeline and/or subsea pipeline. In this relevant variation the invention offers a significant advantage, as repair or replacement of the buried pipeline and/or the subsea pipeline can be very costly.

BRIEF DESCRIPTION OF THE DRAWINGS

The invention will now be illustrated by describing a preferred method according to the invention, and by the accompanying drawing, in which.

DETAILED DESCRIPTION OF THE INVENTION

Figure 1:
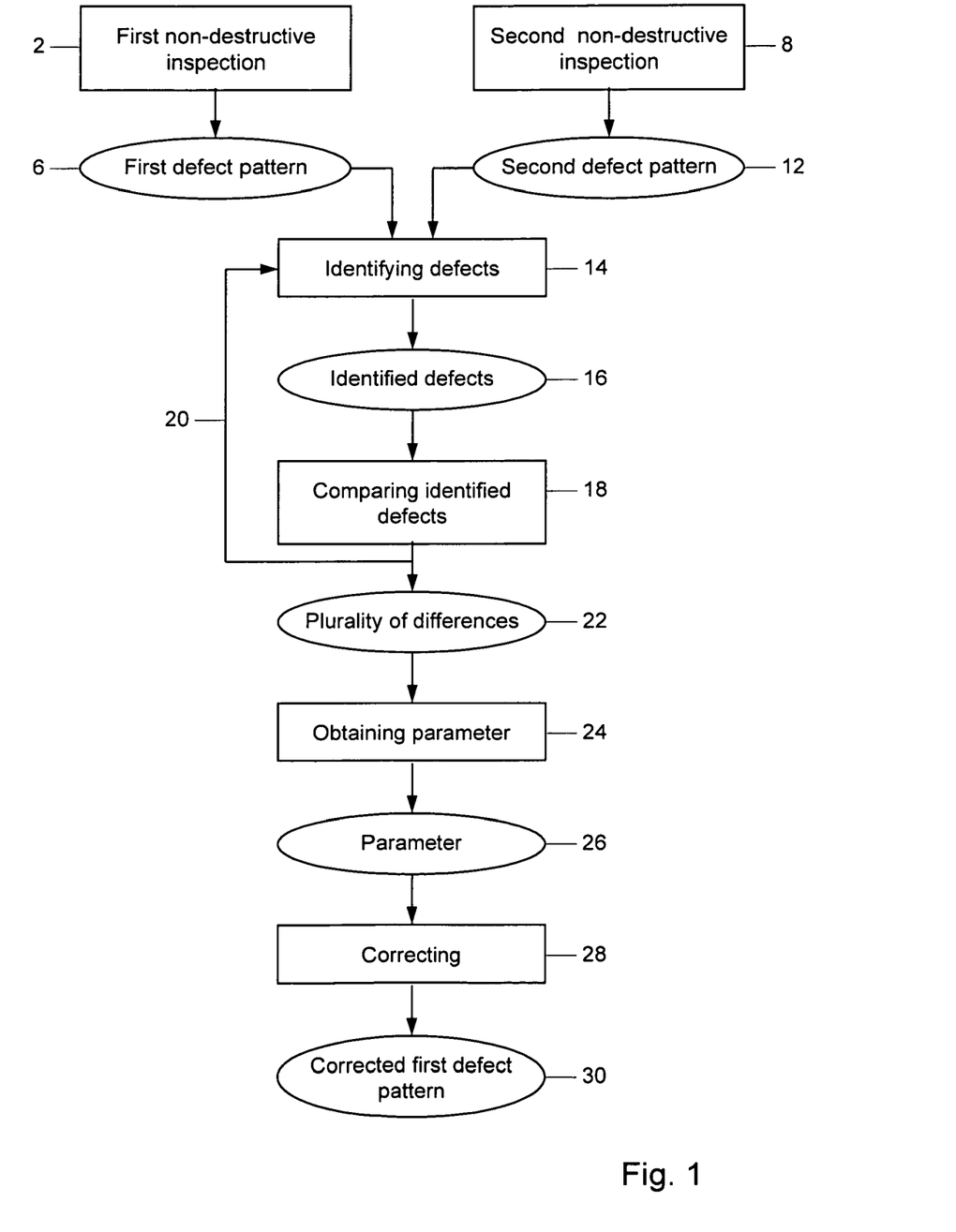
FIG. 1 shows a scheme of a preferred method according to the invention.

FIG. 1 shows a scheme of a preferred method according to the invention for non-destructive inspection of defects in a surface of a pipeline or storage tank. The pipeline can be operated for transport of hydrocarbons such as oil or gas, and the storage tank can be operated for storage of hydrocarbons.

In this preferred method, measurement data are gathered by carrying out an, in-line, first non-destructive inspection 2 using a first way of non-destructive inspection of the pipeline or storage tank. The first way of non-destructive inspection is carried out for inspecting a first part of the surface by moving a first inspection tool along the first part of the surface for determining a first defect pattern 6 that includes dimensions and positions of defects in the first part of the surface. In the preferred method, the first way of non-destructive inspection includes using Magnetic Flux Leakage measurements. The first inspection tool can be arranged for carrying out the MFL measurements. Non-destructive inspection based on MFL measurements yields extend of metal loss of the pipeline or storage tank and a location of this metal loss, being an example of a defect. Metal loss can be caused by corrosion.

The preferred method also includes a second non-destructive inspection 8 by carrying out a second way of non-destructive inspection of a second part of the pipeline by moving a second inspection tool along the second part of the surface for determining a second defect pattern 12 that includes dimensions and positions of defects in the second part of the surface. The second way of non-destructive inspection is carried out using laser profilometry. This method can measure defects very accurately. The second inspection tool can be arranged for carrying out inspection by means of laser profilometry.

The total area of the second part of the surface is substantially smaller than the total area of the first part of the surface. In addition a systematic error of the second way of non-destructive inspection is substantially smaller than a systematic error of the first way of non-destructive inspection. In general it can be stated that in the preferred method, a time needed for carrying out the second way of non-destructive inspection is substantially smaller than a time needed for carrying out the first way of non-destructive inspection. Also, the second part of the surface overlaps with the first part of the surface. This means that at least a portion of the second part of the surface is formed by a portion of the first part of the surface. The first part of the surface can be the pipeline, possibly build out of a number of metal pipes that are welded together, and the second part of the surface can for example be one of these pipes.

In the preferred method, the first way of non-destructive inspection may be carried out before the second way of non-destructive inspection, so that a result of carrying out the first way of non-destructive inspection is used for selecting the second part of the surface. In this way it can for example be achieved that the second defect pattern contains enough defects of various sorts for making a useful comparison with the first defect pattern.

In case the pipeline is a burried pipeline such as a subsea pipeline, the first and second inspection tool are moved through the pipeline along an inside surface of the pipeline. Then, the preferred method according to the invention is also non-destructive for material and/or surrounding objects being present adjacent to the pipeline.

In general, the first and second way of non-destructive inspection are carried out substantially automatically. This has the advantage that human errors are substantially prevented.

The dimensions of the defects of the first and second defect pattern can include at least one of a length, a width, and a depth of the defects. For example, the length is measured along a direction of movement of the first and second inspection tool, the depth is measured transverse to the length direction and transverse to the surface, and the width is measured transverse to both the length direction and the depth direction.

The preferred method further includes identifying 14 a defect 16 of the first defect pattern and a defect 16 of the second defect pattern which represent one and the same defect in the surface. This can be done by means of well known pattern recognition methods wherein the first defect pattern and the second defect pattern are matched so as to locate defects in the first pattern which correspond with defect in the second pattern. The preferred method also includes comparing 18 the dimensions of the defect 16 of the first defect pattern and the defect 16 of the second defect pattern, i.e. the identified defects, which represent one and the same defect so as to obtain a difference in dimensions measured with the first way of non-destructive inspection and the second way of non-destructive inspection respectively. Such identifying 14 and comparing 18 are repeated 20 so as to obtain a plurality of differences 22 and obtaining 24 a parameter 26 representing said differences 22. The preferred method further includes correcting 28 the dimensions and optionally also the positions of defects of the first defect pattern by using the parameter 26. This yields a corrected first defect pattern 30.

Figure 2A:
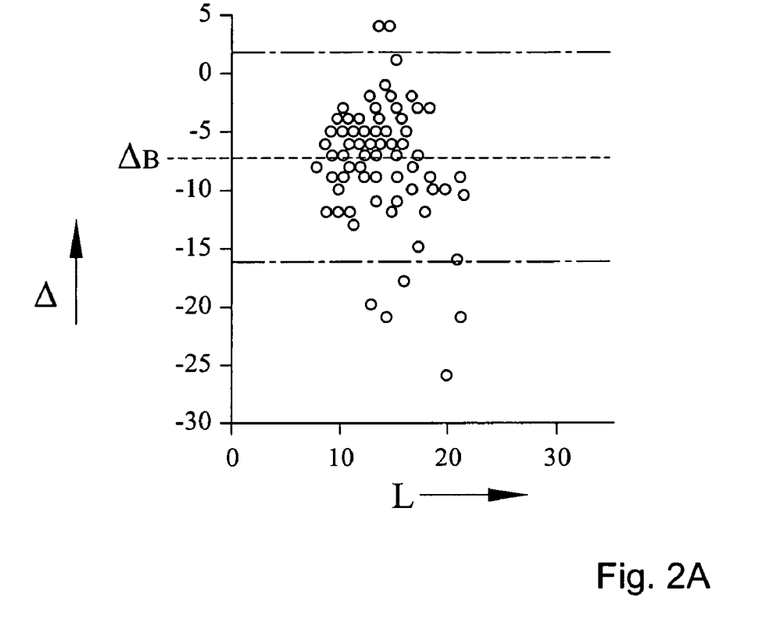
FIG. 2A shows a plot of a difference Δ in a defect length in a first defect pattern and a second defect pattern, versus an average of the defect length in the first and second defect pattern.
Figure 2B:
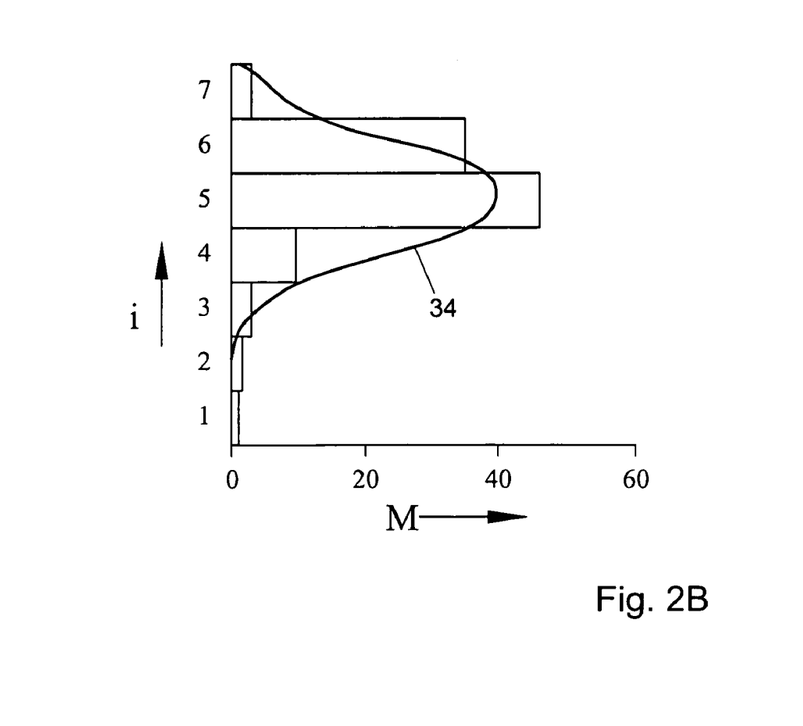
FIG. 2B shows an amount of defects M in each range i.

FIGS. 2A and 2B illustrate a possible way for obtaining 24 the parameter 26 from the plurality of differences 22, according to the preferred method. FIG. 2A shows a plot of the plurality of differences Δ in the defect length L, versus an average of the defect length L in the first and second defect pattern. Each dot represents one physical defect. Units of Δ and L are similar, in this case centimeter. Ranges i of the differences Δ can be defined, and the amount M of defects in each range i of Δ can be counted. FIG. 2A, where Δ=0 would indicate no bias, shows an average bias $\Delta_B$ between the defect length L in the first and second defect pattern. The bias $\Delta_B$, being an example of the parameter 26 of FIG. 1, is largely caused by the systematic error in the first defect pattern as a result of the systematic error in the first way of non-destructive inspection, which is much larger than the systematic error in the second defect pattern.

Figure 3:
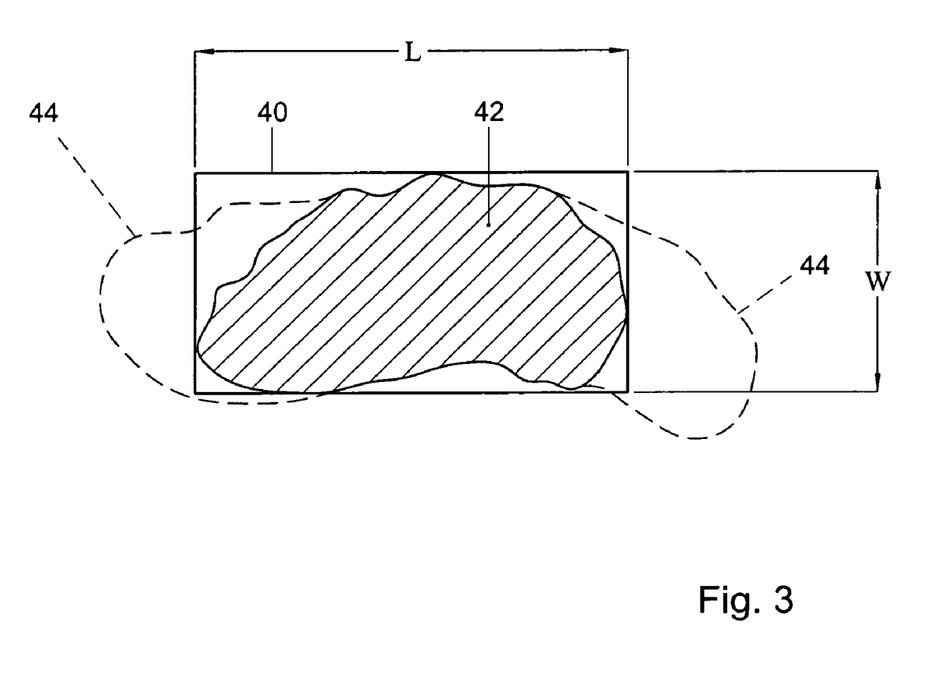
FIG. 3 shows defined boxes.

FIG. 2B shows the amount of defects M in each range i. An average curve 34 can be defined, for example by assuming a normal distribution. The bias $\Delta_B$ can be obtained from the top of the normal distribution. The bias $\Delta_B$ can for example be determined by using a statistical method, such as one or more of a paired t-test, a Wilcoxon signed ranks test, and a passing-bablok method. The preferred method also includes inferring reliability of the bias $\Delta_B$ using the statistical method. In the example of FIGS. 2A and 2B, the bias $\Delta_B$ can be used for correcting the dimensions, in this example the defect length L, of the first defect pattern by using the bias $\Delta_B$. In a similar way, the width, depth and/or positions of defects of the first defect pattern can be corrected, in general using distinct parameters 26. A length of a defect in the first or second pattern can be estimated on the bases of a measured shape of the defect. Based on this shape a box is defined which corresponds with this shape. FIG. 3 shows a box 40, which encloses a defect 42 of the first or second defect pattern. The box 40 has a length L and a width W corresponding to a width and length of the enclosed defect 42. The box 40 may have a depth as well, although in the preferred method of FIG. 3 only two-dimensional boxes 40 are used. Around the defect 42, the MFL inspection can show defect indications 44, possibly being a measurement error or a very shallow defect. In order to eliminate such shallow or false defects, a threshold value for the depth may be used, were a measured defect is regarded as being an error if the measured depth is smaller than the threshold value. Preferably such boxes are defined in the first defect pattern each of which encloses one of the defects of the first defect pattern for more than 50%, more than 80%, and/or 100%. These boxes have a length, width and possibly a depth, corresponding respectively to a length, width, and depth of the enclosed defect. Furthermore such boxes are defined in the second defect pattern each of which encloses one of the defects of the second defect pattern for more than 50%, more than 80%, and/or 100%. These boxes have a length, width and possibly a depth corresponding respectively to a length, width, and depth of the enclosed defect. Now based on the positions and dimensions of the boxes in the first defect pattern and the boxes in the second defect pattern the method includes identifying at least one box of the first defect pattern and at least one box of the second defect pattern which represent one and the same defect. This can be done by pattern recognition techniques as discussed above wherein a pattern of boxes belonging to the first defect pattern is matched with a pattern of boxes belonging to the second defect pattern. Further the preferred method includes comparing the dimensions and optionally also the positions of the identified boxes which represent one and the same defect so as to obtain a difference in dimensions and optionally also the positions measured with the first way of non-destructive inspection and the second way of non-destructive inspection respectively. The differences are obtained for a plurality of defects and the at least one parameter is obtained as discussed above.

When determining the second defect pattern and the first defect pattern, multiple defects in one of these defect patterns may overlap with one and the same defect in the other defect pattern. In the preferred method, such multiple defects are aggregated as one defect. In order to determine whether such multiple defects overlap, it may be determined whether the boxes 40 that enclose the multiple defects overlap with a box 40 of the other defect pattern.

The preferred method includes classifying the defects of the first defect pattern in a plurality of defect categories. Classifying the defects of the first defect pattern can be based on the dimensions of the defects. Based on these dimensions, various categories can be defined.

Figure 4:
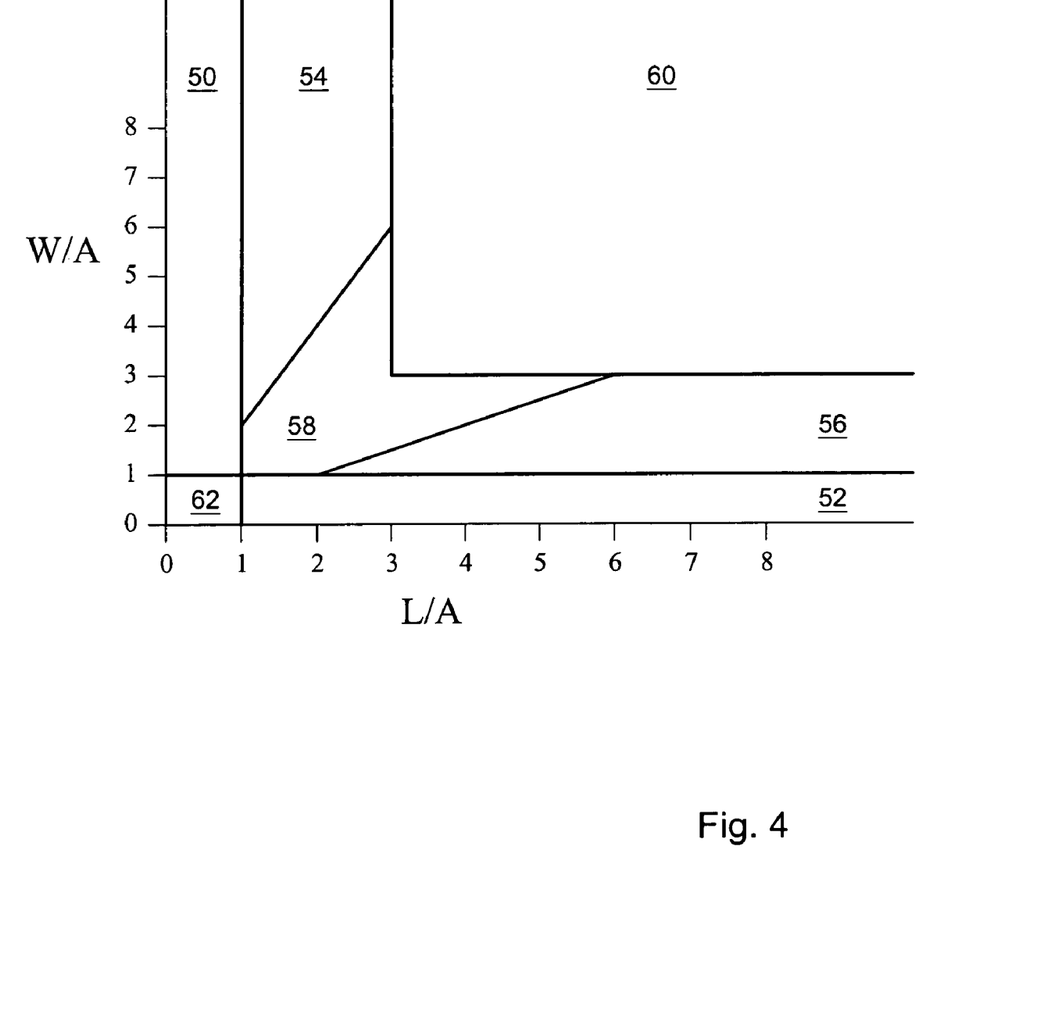
FIG. 4 shows a plot defining seven categories that can be used for classifying the defects.

FIG. 4 shows a plot defining seven categories that can be used for classifying the defects. These categories are circumferential slotting 50, axial slotting 52, circumferential grooving 54, axial grooving 56, pitting 58, general 60, and pinhole 62. Along the axes of FIG. 4 are the defect length L and the defect width W, both normalised by a thickness A of the wall of the pipeline or storage tank.

In the preferred method, correcting 30 is carried out with at least one separate parameter 26 for each category. This separate parameter is obtained as discussed above per category of defects. First defects of the first defect pattern which correspond to defect of the second defect pattern may be determined as discussed above. This results in a accumulation of defects. Than from this accumulation of defects a sub accumulation of defects is obtained which only comprises defects of the first defect pattern which belong to a first category and corresponding defects of the second defect pattern. Based on these defects at least one parameter for the first category is obtained as discussed above. In this example one parameter is obtained which represents a bias in the length of defects of the first pattern belonging to the first category and one parameter is obtained which represents a bias in the width of defects of the first pattern belonging to the first category. Subsequently each of the defects of the first pattern which belong to the first category are corrected by means of these two parameters. The first category may for example be axial slotting. A second category may for example any of the other referred to categories or all remaining defects not belonging to the category of axial slotting. The same process as discussed for the first category is carried out for the second category. In this case from the accumulation of defects a sub accumulation of defects is obtained which only comprises defects of the first defect pattern which belong to the second category and corresponding defects of the second defect pattern. Based on these defects at least one parameter for the second category is obtained as discussed above. In this example one parameter is obtained which represents a bias in the length of defects of the first pattern belonging to the second category and one parameter is obtained which represents a bias in the width of defects of the first pattern belonging to the second category. Subsequently each of the defects of the first pattern which belong to the second category are corrected by means of these two parameters. The same process may be carried out for a possible third, fourth etc. category.

Alternatively both the defects of the first defect pattern as well as the defects of the second defect pattern are divided into categories of the types as discussed above. In this alternative method, correcting 30 is also carried out with at least one separate parameter 26 for each category. This separate parameter is obtained as discussed above per category of defects. First defects of the first defect pattern which correspond to defect of the second defect pattern may be determined as discussed above. This results in an accumulation of defects. Than from this accumulation of defects a sub accumulation of defects is obtained which only comprises defects of the second defect pattern which belong to a first category and corresponding defects of the first defect pattern. Based on these defects at least one parameter for the first category is obtained as discussed above. In this example one parameter is obtained which represents a bias in the length of defects of the first pattern belonging to the first category and one parameter is obtained which represents a bias in the width of defects of the first pattern belonging to the first category. Subsequently each of the defects of the first pattern which belong to the first category are corrected by means of these two parameters. The first category may again for example be axial slotting. A second category may for example any of the other referred to categories or all remaining defects not belonging to the category of axial slotting. The same process as discussed for the first category is carried out for the second category. In this case from the accumulation of defects a sub accumulation of defects is obtained which only comprises defects of the second defect pattern which belong to the second category and corresponding defects of the first defect pattern. Based on these defects at least one parameter for the second category is obtained as discussed above. In this example one parameter is obtained which represents a bias in the length of defects of the first pattern belonging to the second category and one parameter is obtained which represents a bias in the width of defects of the first pattern belonging to the second category. Subsequently each of the defects of the first pattern which belong to the second category are corrected by means of these two parameters. The same process may be carried out for a possible third, fourth etc. category.

In the above examples defects of the first and second defect pattern which correspond to each other are determined based on the full first and second defect pattern comprising all defects. It is however also possible to first determine a sub accumulation of defects of the first pattern which belong to a first category and than based on these defects determine the defects of the second pattern which correspond to the defects of the first pattern belonging to the first category. In a similar way defects of the first pattern belonging to a second category may be determined and defects of the second category may be determined which correspond with these defects. Once corresponding defects belonging to one and the same category are determined at least one parameter for such category may be determined as discussed above for correcting defects of the first category belonging to such category. The same applies to defects belonging to other categories.

As systematic errors of MFL-measurements in general depend on the dimensions of the defect, a better correction can be achieved that using just a single correction factor for all defects.

In a more preferred method according to the invention, the preferred method includes validating the at least one parameter 26. Such validating can include carrying out the second way of non-destructive inspection for a third part of the pipeline, to obtain a third defect pattern that includes dimensions and positions of defects in the third part of the surface, wherein the total area of the third part of the surface is smaller than the total area of the first part of the surface and the third part of the surface overlaps with the first part of the surface. At least the part of the first defect pattern which overlaps with the third part of the surface is corrected with the at least one parameter which is obtained as discussed above. This results in a corrected first defect pattern. Than the corrected first defect pattern is compared with the third defect pattern and it is verified that the differences obtained between defects of the corrected first pattern and the third pattern are generally smaller than the differences obtained when using the uncorrected first pattern and the second defect pattern, in accordance with a statistic criterium.

It is also possible that at least one parameter is determined which represents the differences between the defects of the corrected first pattern and the defects of the third pattern in the same manner as discussed above for the differences between the defects of the first pattern and defects of the second pattern. This at least one parameter is than compared with the same parameter representing differences between defects of the first pattern and defects of the second pattern. It is verified that the at least one parameter which represents the differences between the defects of the corrected first pattern and the defects of the third pattern represents smaller differences than the at least parameter which represents the differences between the defects of the first pattern and the defects of the second pattern.

The above verification may be carried out per category of defects. Hence for each category it may be verified that the at least one parameter which represents the differences between the defects of the corrected first pattern and the defects of the third pattern and belonging to a certain category represents smaller differences than the at least parameter which represents the differences between the defects of the first pattern and the defects of the second pattern and belonging to the same category.

Verifying can include verifying that the at least one parameter such as the bias $\Delta_B$ when using the third defect pattern and the corrected first pattern is substantially, for example more than 1.2 times, or more than two times, smaller than the at least one parameter such as the bias $\Delta_B$ when using the second defect pattern and the uncorrected first pattern. The same applies to other parameters representing other biases.

The preferred method can for example be applied to above-ground storage tanks, in particular above-ground storage tanks that need to meet requirements of the American Petroleum Institute (API) described in API 650 and/or API 620 standards.

In an alternative method according to the invention, the first way of non-destructive inspection can include using ultrasonic measurements or electromagnetic measurements in general. The first and second defect pattern may also include information about a shape of the defect. The defects of the first and second defect pattern may also be a result of mechanical damage, erosion, and/or fracturing.

The invention is not limited to any embodiment herein described and, within the purview of the skilled person, modifications are possible which should be considered within the scope of the appended claims. Equally all kinematic inversions are considered inherently disclosed and to be within the scope of the present invention. The use of expressions like: "preferably", "preferred", "in particular" etc. is not intended to limit the invention. Features which are not specifically or explicitly described or claimed may be additionally included in the structure according to the present invention without deviating from its scope.

The invention claimed is:

1. A method for non-destructive inspection of defects in a surface of a pipeline or storage tank for hydrocarbon transport or storage, including the steps of:
   a) carrying out a first way of non-destructive inspection of a first part of the surface by moving a first inspection tool along the first part of the surface for determining a first defect pattern that includes dimensions and positions of defects in the first part of the surface;
   b) carrying out a second way of non-destructive inspection of a second part of the surface by moving a second inspection tool along the second part of the surface for determining a second defect pattern that includes dimensions and positions of defects in the second part of the surface, wherein a total area of the second part of the surface is smaller than a total area of the first part of the surface and the second part of the surface overlaps with the first part of the surface, and wherein a systematic error of the second way of non-destructive inspection is smaller than a systematic error of the first way of non-destructive inspection;
   c) identifying at least one defect of the first defect pattern and at least one defect of the second defect pattern which represent one and the same defect;
   d) comparing the dimensions and optionally also the positions of the identified defects in step c) which represent one and the same defect so as to obtain a difference in dimensions and optionally also in the positions measured with the first way of non-destructive inspection and the second way of non-destructive inspection respectively;

e) repeating steps c) and d) so as to obtain a plurality of differences and obtaining at least one parameter representing said differences; and f) correcting the dimensions and optionally also the positions of defects of the first defect pattern by using the at least one parameter obtained in step e).

2. The method according to claim 1, wherein the first and second way of non-destructive inspection are carried out substantially automatically.

3. The method according to claim 1, wherein the first way of non-destructive inspection is an in-line inspection method.

4. The method according to claim 1, including moving the first and/or second inspection tool along the inside and/or outside surface of the pipeline or storage tank.

5. The method according to claim 1, wherein the first way of non-destructive inspection includes using Magnetic Flux Leakage measurements.

6. The method according to claim 1, wherein the first way of non-destructive inspection includes using ultrasonic measurements.

7. The method according to claim 1, wherein the first way of non-destructive inspection includes using electromagnetic measurements.

8. The method according to claim 1, wherein the second way of non-destructive inspection includes inspection by means of a laser.

9. The method according to claim 8, wherein the second way of non-destructive inspection includes laser profilometry.

10. The method according to claim 1, wherein the total area of the second part of the surface is more than two times, more than ten times, more than fifty times, more than a hundred times, and/or more than a thousand times smaller than the total area of the first part of the surface.

11. The method according to claim 1, wherein the systematic error of the second way of non-destructive inspection is more than 1.2 times, more than 1.5 times, more than two times, more than three times, more than five times, more than ten times, and/or more than twenty times smaller than a systematic error of the first way of non-destructive inspection.

12. The method according to claim 1, wherein a time needed for step b) is substantially smaller than a time needed for step a).

13. The method according to claim 1, wherein step a) is carried out before step b) and a result of carrying out the first way of non-destructive inspection is used for selecting the second part of the surface.

14. The method according to claim 1, wherein the dimensions of the defects of the first and/or second defect pattern include at least one of a length, a width, and a depth of the defects.

15. The method according to claim 1, wherein identifying defects in step c) is carried out using pattern matching techniques.

16. The method according to claim 1, wherein step e) includes using a statistical method, such as at least one of a paired t-test, a Wilcoxon signed ranks test, and a passing-bablok method, for obtaining the at least one parameter from the plurality of differences.

17. The method according to claim 16, including inferring reliability of the at least one parameter using the statistical method.

18. The method according to claim 1, wherein the at least one parameter includes at least one dimension correction number for correcting the dimensions of the defects of a first defect pattern and optionally a position correction number for correcting the position of the defects of a first defect pattern.

19. The method according to claim 1, including classifying the defects of the first defect pattern and optionally the defects of the second defect pattern in a plurality of defect categories.

20. The method according to claim 19, wherein the classification of the defects of the first defect pattern and the optional classification of the defects of the second defect pattern in the plurality of defect categories is based on the dimensions of the defects.

21. The method according to claim 19, wherein steps d) and e) are carried out while being limited to defects of the first defect pattern which belong to a first category of the plurality of categories so as to obtain at least a first parameter for the first category and wherein steps d) and e) are carried out while being limited to defects of the first defect pattern which belong the a second category of the plurality of categories so as to obtain at least a second parameter for the second category and wherein step f) includes correcting the dimensions and optionally the positions of the defects of the first defect pattern belonging to the first category by using the at least one first parameter for the first category and correcting the dimensions and optionally the positions of the defects of the first defect pattern belonging to the second category by using the at least one second parameter for the second category.

22. The method according to claim 19, wherein steps d) and e) are carried out while being limited to defects of the second defect pattern which belong to a first category of the plurality of categories so as to obtain at least a first parameter for the first category and wherein steps d) and e) are carried out while being limited to defects of the second defect pattern which belong to a second category of the plurality of categories so as to obtain at least a second parameter for the second category and wherein step f) includes correcting the dimensions and optionally the positions of the defects of the first defect pattern belonging to the first category by using the at least one first parameter for the first category and correcting the dimensions and optionally the positions of the defects of the first defect pattern belonging to the second category by using the at least one second parameter for the second category.

23. The method according to claim 1, wherein step f) yields a corrected first defect pattern.

24. The method according to claim 23, includes clustering interacting neighbouring defects of the corrected first defect pattern, and using predetermined interaction criteria for deciding whether neighbouring defects interact.

25. The method according to claim 23, including determining a failure pressure using the corrected first defect pattern after clustering.

26. The method according to claim 23, including validating the at least one parameter.

27. The method according to claim 26, wherein validating includes the steps of:

g) carrying out the second way of non-destructive inspection for a third part of the pipeline by moving the second inspection tool along the third part of the surface for determining a third defect pattern that includes dimensions and positions of defects in the third part of the surface, wherein a total area of the third part of the surface is smaller than the total area of the first part of the surface, the third part of the surface overlaps with the first part of the surface and wherein the third part differs from the second part;

h) identifying at least one defect of the corrected first defect pattern and at least one defect of the third defect pattern which represent one and the same defect;

i) comparing the dimensions and optionally also the positions of the identified defects in step h) which represent one and the same defect so as to obtain a difference in dimensions and optionally also in the positions measured with the first way of non-destructive inspection and the second way of non-destructive inspection respectively;

j) repeating steps h) and i) so as to obtain a plurality of differences; and k) verifying that the differences obtained in step j) are generally smaller than the differences obtained in step e) in accordance with a statistic criterium.

28. The method according to claim 27, wherein in step j) at least one parameter is obtained representing the differences obtained in step j) wherein the at least one parameter which is obtained in step j) is obtained in the same manner as the at least one parameter which is obtained in step e) and wherein in step k) the differences are verified that the parameter which is obtained in step k) represents generally smaller differences than the parameter which is obtained in step e).

29. The method according to claim 1, wherein in determining the second defect pattern multiple defects of the second defect pattern that overlap with one and the same defect of the first defect pattern are aggregated as one defect of the second defect pattern.

30. The method according to claim 1, wherein in determining the first defect pattern multiple defects in the first defect pattern that overlap with one and the same defect of the second defect pattern are aggregated as one defect of the first defect pattern.

31. The method according to claim 1, including defining first boxes in the first defect pattern each of which encloses one of the defects of the first defect pattern for more than 50%, more than 80%, and/or 100%, the first boxes having a length, width and possibly a depth corresponding respectively to a length, width, and depth of the enclosed defect and defining second boxes in the second defect pattern each of which encloses one of the defects of the second defect pattern for more than 50%, more than 80%, and/or 100%, the second boxes having a length, width and possibly a depth corresponding respectively to a length, width, and depth of the enclosed defect.

32. The method according to claim 31, wherein step c) includes identifying at least one box of the first defect pattern and at least one box of the second defect pattern which represent one and the same defect; and wherein step d) includes comparing the dimensions and optionally also the positions of the identified boxes in step c) which represent one and the same defect so as to obtain a difference in dimensions and optionally also the positions measured with the first way of non-destructive inspection and the second way of non-destructive inspection respectively.

33. The method according to claim 1, including hydrotesting of the pipeline.

34. The method according to claim 1, including mitigation of the pipeline or storage tank, preferably including repair and/or replacement of the pipeline or storage tank.

35. The method according to claim 1, wherein the defect is caused by cracking, by mechanical damage, and/or by corrosion.

36. The method according to claim 1, wherein the pipeline is a burried pipeline and/or subsea pipeline.

37. The method according to claim 1, wherein the surface is a metal surface.

38. The method according to claim 1, wherein the pipeline is a carbon steel pipeline.

39. The method according to claim 1, wherein the storage tank is an above-ground storage tank.

40. The method according to claim 1, including assessment and/or reporting of the integrity of the pipeline or storage tank according to the API Standard 1163.

* * * * *